United States Patent [19]

Shin et al.

[11] 4,226,228
[45] Oct. 7, 1980

[54] MULTIPLE JOINT RETRACTOR WITH LIGHT

[76] Inventors: Hee J. Shin; Jung H. Shin, both of 195 Haggerty Ave., Phillipsburg, N.J. 08865

[21] Appl. No.: 957,008

[22] Filed: Nov. 2, 1978

[51] Int. Cl.³ .............................................. A61B 1/06
[52] U.S. Cl. ...................................... 128/20; 128/23
[58] Field of Search ...................... 128/3–6, 128/9–20

[56] References Cited

U.S. PATENT DOCUMENTS

| 104,874 | 6/1870 | Osborn | 128/15 |
|---|---|---|---|
| 878,917 | 2/1908 | Wappler | 128/7 |
| 1,767,267 | 6/1930 | Wappler | 128/7 |
| 2,079,233 | 5/1937 | Wappler | 128/7 |
| 2,840,070 | 6/1958 | Tofflemire | 128/11 |
| 3,190,286 | 6/1965 | Stokes | 128/6 |
| 3,642,352 | 2/1972 | Beach | 128/303.1 X |
| 3,799,151 | 3/1974 | Fukaumi et al. | 128/6 |
| 3,882,855 | 5/1975 | Schulte et al. | 128/20 |
| 3,890,960 | 6/1975 | Wunsch nee Kuhn et al. | 128/16 |
| 4,048,987 | 9/1977 | Hurson | 128/20 |
| 4,078,555 | 3/1978 | Takahashi | 128/4 |

*Primary Examiner*—Robert W. Michell
*Assistant Examiner*—Jeffrey W. Tayon
*Attorney, Agent, or Firm*—Clarence A. O'Brien; Harvey B. Jacobson

[57] ABSTRACT

A surgical implement is disclosed for performing in combination a retracting and illuminating function within body cavities formed during surgery. The retraction function is performed by a blade, which can be segmented for flexible bending, mounted generally at right angles to a support shaft manipulatable by a handle. Miniature lamps present in the blade and powered by small batteries located in the handle perform the illumination function within the body cavity around which the retraction function is simultaneously performed.

9 Claims, 6 Drawing Figures

MULTIPLE JOINT RETRACTOR WITH LIGHT

BACKGROUND OF THE INVENTION

1. Field of the Invention

The invention relates to a surgical implement for use during a surgical operation when a cavity is formed in the anatomy of a patient. More particularly, the device pertains to a solution for problems recognized in the surgical field pertaining to provision of adequate illumination of the working region where a surgeon operates.

2. Description of the Prior Art

Attempts to provide illumination have included overhead or relatively distant fixedly mounted lights to provide general illumination, but such devices create shadows or regions of fluctuating brightness when surgeons or others present move about. Furthermore, such lights are difficult to focus to the region of operation, and are not easily adjusted as the need for illumination changes during the progress of the surgical procedure.

Other prior illuminating devices are not capable of easy sterilization by standard surgical methods, such as by passing through an autoclave. Other types of relatively high intensity lighting, such as a standard incandescent bulb mounted in a conventional receptacle socket can generate excessive heat which could damage or deleteriously affect living tissues, or which are excessively bulky and inconvenient due to the requirement for a connection by means of an electrical cord to an external source of power. Moreover, no retracting function is possible with such devices.

SUMMARY OF THE INVENTION

Accordingly, it is an object of the present invention to provide a surgical implement capable of performing a retracting function and an illuminating function within a cavity in the anatomy of a patient during surgery.

Another object of the invention is to provide an illuminated retractor having linked segments movable for adjustment of the blade of the retractor in order to control the illumination of the cavity and gripping of the cavity edge.

Another object of the invention is to provide a surgical implement performing both retracting and illuminating functions, and which is conveniently sterilized by standard hospital techniques in a conventional autoclave.

Yet a further object is to provide a surgical retractor with illuminating means which delivers adequate illumination for conducting a surgical procedure, without damage or deleterious effect upon living tissues.

Still another object is to provide a multiple joint interlocking retractor easily manufactured from common materials by well-known techniques, and which is convenient to use, occupies a minimum of space when in use, and in addition, is durable, efficient and reliable when used for its intended function.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

Figure 1:
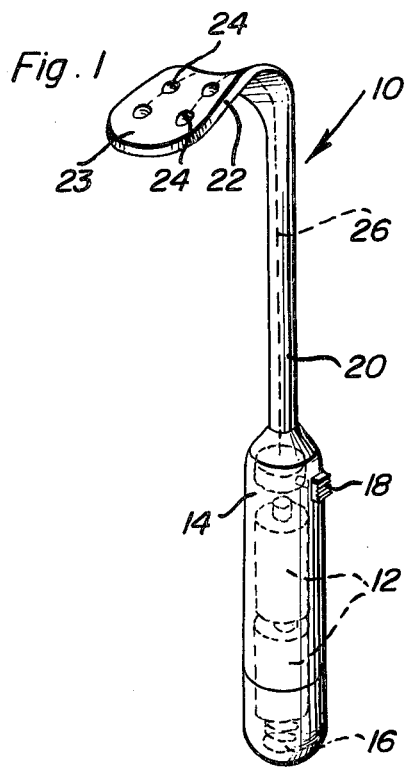
FIG. 1 is a perspective view of a lighted retractor of the present invention, showing in phantom outline a pair of batteries enclosed within the handle.

FIG. 1 discloses a fixed illuminated retractor designated generally by the numeral 10 with batteries 12 being contained in handle 14 which also is provided with spring 16 for maintaining electrical contact, and with switch 18, for opening and closing the electrical circuit, one leg of which can comprise the framework of the device, if the framework is constructed of an electrically conductive material, such as metal. Shaft 20 connects handle 14 with blade 22, which contains on inward surface 23 the lighting means comprising electric lamps 24. When shaft 20 functions as a leg of the electrical circuit, shaft 20 is hollow and contains a single insulated wire 26 terminating at one end at a contact (not shown) at the interior portion of switch 18, and terminating at the opposite end in blade 22 at an electrical contact of lamps 24, which can be connected either in parallel, with suitable branching of wire 26, or in series, with connections between individual lamps 24.

Many prior art patents describe methods for mounting small electrical lamps in surgical implements and certain of these disclosures are incorporated in this application by reference to the following patents. U.S. Pat. No. 1,767,025, issued June 24, 1930, to Wappler, shows a cystoscope without mechanical movement or articulated parts, disclosing a lamp 16 mounted in an extension 15 of the device. Another disclosure of mounting means is found in the Wappler U.S. Pat. No. 878,917, issued Feb. 11, 1908, and in the endoscope disclosed by Takahashi in U.S. Pat. No. 4,078,55, issued Mar. 14, 1978.

Instead of utilizing the framework of the device of FIG. 1 as a leg of the electrical circuit, two insulated wires can be used, each carrying current to lamps 24 from batteries 12. Such a configuration would be required, for example, if shaft 20 is constructed of a nonconductive material, such as could be preferable in certain surgical procedures where some danger from the presence of an electrical conductor might exist during the surgical operation.

Figure 2:
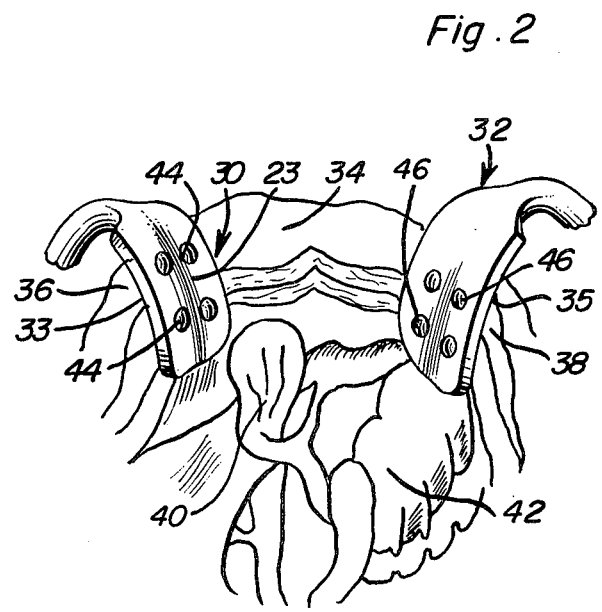
FIG. 2 is an enlarged, perspective view of a surgical cavity in which a pair of lighted retractors of the present invention are in use.

In FIG. 2, retractors 30 and 32 are shown in use, each being of the type and construction shown in FIG. 1. A body cavity with walls 34 is pulled outwardly by the outward surface 33 of the retractor 30 at point 36, and is pulled outwardly by the outward surface 35 of retractor 32 at point 38. Organs 40 and 42 are representative of internal body parts undergoing examination or other steps in a surgical procedure. It is seen from FIG. 2 that organ 40 is illuminated by each of the bulbs 44 on the inward surface 23 of retractor 30 and bulbs 46 on retractor 32, thereby concentrating and projecting light on organ 40 from two different directions, while maintaining a clear field of vision for a surgeon standing behind cavity wall 34.

Figure 3:
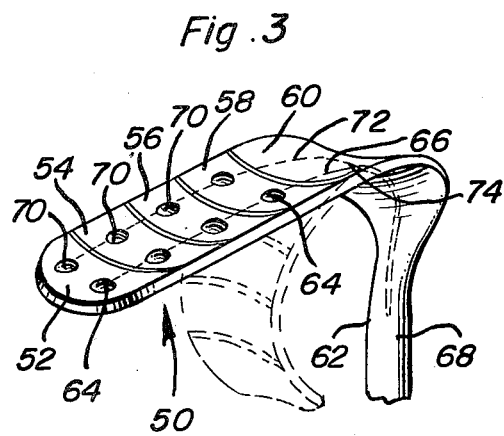
FIG. 3 is a fragmental, enlarged view of the blade portion of a multiple joint interlocking lighted retractor, showing in phantom outline an alternative positioning of the blade.

FIG. 3 shows the blade portion 50 of a multiple joint interlocking retractor, with individual segments 52, 54, 56 and 58 linked together, with segment 58 linked to lip 60 formed as part of the framework including shaft 62. Flexibility of the segments is indicated in FIG. 3 by the phantom outline showing an alternative positioning of segments 52, 54, 56 and 58, affording a different pattern of illumination and a different contour for conformance with the body cavity with which the segments make contact. Lamps 64 are shown connected in series from a branch 66 of electrical cord 68, and lamps 70 are similarly connected in series from branch 72, branches 66 and 72 joining cord 68 at junction 74. Each of the electrical cords is insulated from its surroundings, and the framework provides a leg for return of electrical current to the batteries (not shown in FIG. 3). Alternatively, as in the case of the fixed illuminated retractor of FIG. 1, a duplicate set of insulated wires can be used to return current to the source of electrical power in the handle.

Disclosure has been made in the prior art of means for flexible linkage of segments in surgical implements. For example, Stokes in U.S. Pat. No. 3,190,286, issued June 22, 1965, shows a segmented flexible endoscope with a plurality of small pivot elements between the segments, and control means are shown for flexing the device by means of a pivoting action similar to a universal joint. Another known method of pivoting sections of an optical device is shown in U.S. Pat. No. 3,642,352, issued Feb. 15, 1972, to Beach, where a manipulating device incorporating three compound joints utilizes ball-bearings to provide pivotal movement. A controllably bendable tube section of an endoscope is shown by Fukaumi, et al., in U.S. Pat. No. 3,799,151, issued Mar. 26, 1974, where an endoscope is shown with control possible over various curvatures into which the tube can be bent when inserted within a living body. Yet another method of pivoting sections of a device is shown in U.S. Pat. No. 2,079,233, issued May 4, 1937, to Wappler, where a pivotal extension of a telescopic tube can be adjusted by the operator. The Fukaumi, et al. patent, the Wappler '233 patent, and the Stokes patent all provide for a current carrying wire passing across joints between adjacent segments. In the present invention, any of the conventional techniques, such as are illustrated by these patents, for linking flexible segments of a surgical implement while carrying current between segments, can be successfully used. Once the retractor is in place in a certain position, however, the joints should remain firm. There should also be a releasing mechanism when it becomes necessary to change the position of the segments of the multiple joint interlocking retractor. One such locking and releasing mechanism is illustrated by the control mechanism described in the Fukaumi et al patent.

Figure 4:
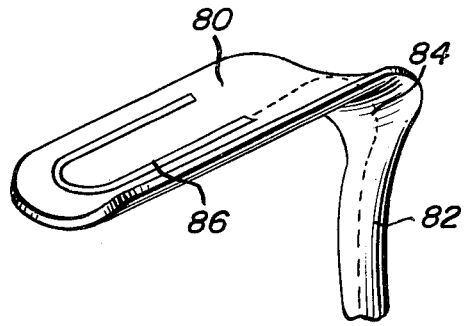
FIG. 4 is an enlarged, fragmental perspective view of the blade portion of a second embodiment of the rigid lighted retractor, showing an alternative manner of placement of lighting means.

In FIG. 4, another embodiment of a fixed illuminated retractor is illustrated, where blade 80 is connected to shaft 82, and electrical cord 84 brings current to an illuminating trough 86, in the same manner as described above in connection with FIG. 1. Illuminating trough 86 preferably has arranged along its length a plurality of connected electrical sockets, each adapted to receive a small electric lamp to provide illumination along the length of trough 86. Alternatively, tubular illuminating means can be installed in trough 86, such as a tubular U-shaped incandescent lamp containing a single filament along its length. Other lighting arrangements conventional in the art can also be employed within trough 86 to direct light upwardly from blade 80.

Figure 5:
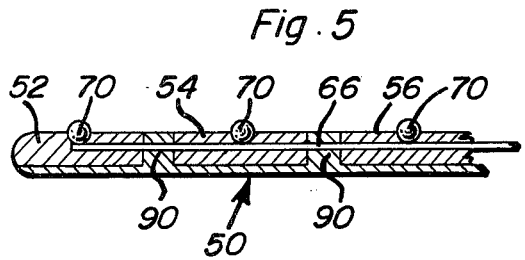
FIG. 5 is a fragmentary, longitudinal sectional view of the distal end of the blade portion of the retractor of FIG. 3.
Figure 6:
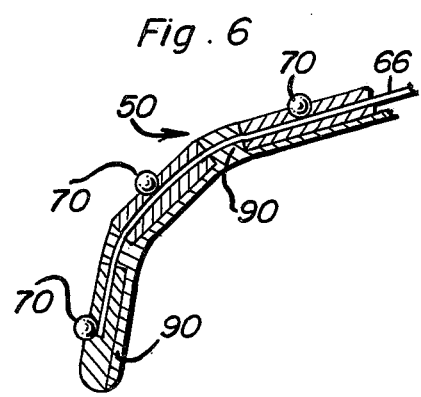
FIG. 6 is a fragmentary, longitudinal sectional view of the device of FIG. 5, showing the blade alternatively positioned after flexing to the configuration shown in phantom in FIG. 3.

In FIGS. 5 and 6 an embodiment of the invention is shown wherein blade portion 50 is made up of spaced transverse rigid segments 52, 54 and 56 linked together by bridging material 90, which can be manually flexible so that blade portion 50 can be manipulated to any desired direction and maintain a continuous surface. Segments 52, 54 and 56 can be joined by conventional techniques, such as by welding or adhesion, with use of flexible aluminum or tin as bridging material 90. Segments 52, 54 and 56 can be made from a suitable surgical material, such as stainless steel.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A surgical retractor for use within a surgical cavity, the retractor comprising retracting means and illuminating means, said retracting means comprising an inward surface and an outward surface, said outward surface conformingly contacting said cavity, said illuminating means comprising a plurality of electric lamps held in electrical contact by mounting means located upon said inward surface for directing illumination within said cavity, said mounting means being connected by electrical conductor means to a source of electric power, said retracting means comprising a plurality of flexible segments adjustably connected at pivotal connecting joints so as to afford a different pattern of illumination and a different contour for conformance with the surgical cavity.

2. The surgical retractor of claim 1, wherein said retracting means is an elongated blade rigidly attached to a straight shaft affixed at its distal end to a handle.

3. The surgical retractor of claim 2, wherein said blade projects outwardly from said shaft, and said inward surface has a concave curvature substantially along its longitudinal extent.

4. The surgical retractor of claim 3, wherein said mounting means comprises a corresponding plurality of electrical sockets, said source of electric power is a dry cell battery, and said conductor means is an insulated electric wire connecting said sockets in circuit with a manual switch and said dry cell battery.

5. The surgical retractor of claim 4, wherein said blade and said shaft comprise a return leg for conduction of electric current between said sockets and said dry cell battery.

6. The surgical retractor of claim 1 wherein said joints comprise a manually flexible bridging material.

7. The surgical retractor of claim 6 wherein said bridging material is selected from a metal in the group consisting of aluminum and tin.

8. The surgical retractor of claim 7 wherein said segments are welded to said bridging material.

9. The surgical retractor of claim 6 wherein said plurality of segments comprises spaced transverse rigid segments containing said mounting means, said segments being linked together by said flexible bridging material, said rigid segments and bridging material forming a continuous surface at all contours of said retracting means.

* * * * *